United States Patent
Hellstrom et al.

(10) Patent No.: US 9,463,222 B2
(45) Date of Patent: *Oct. 11, 2016

(54) METHODS FOR TREATMENT OF COMPLICATIONS OF PREMATURITY COMPRISING ADMINISTRATION OF IGF-I AND IGFBP-3

(71) Applicant: Premacure AB, Uppsala (SE)

(72) Inventors: Ann Hellstrom, Hovas (SE); Chatarina Lofqvist, Askim (SE); Lois Smith, West Newton, MA (US)

(73) Assignee: PREMACURE AB, Uppsala (SE)

(*) Notice: Subject to any disclaimer, the term of this patent is extended or adjusted under 35 U.S.C. 154(b) by 0 days.

This patent is subject to a terminal disclaimer.

(21) Appl. No.: 14/617,520

(22) Filed: Feb. 9, 2015

(65) Prior Publication Data

US 2015/0216943 A1    Aug. 6, 2015

Related U.S. Application Data

(60) Continuation of application No. 13/949,750, filed on Jul. 24, 2013, now abandoned, which is a division of application No. 12/596,572, filed as application No. PCT/SE2008/050441 on Apr. 18, 2008, now Pat. No. 8,518,877.

(60) Provisional application No. 60/923,963, filed on Apr. 18, 2007.

(51) Int. Cl.
  *A61K 38/30* (2006.01)
  *A61K 38/17* (2006.01)

(52) U.S. Cl.
  CPC .......... *A61K 38/30* (2013.01); *A61K 38/1709* (2013.01); *A61K 38/1754* (2013.01)

(58) Field of Classification Search
  None
  See application file for complete search history.

(56) References Cited

U.S. PATENT DOCUMENTS

| | | |
|---|---|---|
| 5,187,151 A | 2/1993 | Clark et al. |
| 5,473,054 A | 12/1995 | Jameson et al. |
| 6,251,865 B1 | 6/2001 | Clark et al. |
| 2004/0053838 A1 | 3/2004 | Smith et al. |

FOREIGN PATENT DOCUMENTS

| | | | |
|---|---|---|---|
| JP | 2004-528529 | | 9/2004 |
| SE | WO 02/43578 | * | 6/2002 |
| WO | WO 95/04076 | | 2/1995 |
| WO | WO 96/40736 | | 12/1996 |
| WO | WO 2007/011926 | | 1/2007 |

OTHER PUBLICATIONS

Baxter et al., "Growth hormone-dependent insulin-like growth factor (IGF) binding protein from human plasma differs from other human igf binding proteins,"*Biochem. Biophys. Res. Comm.*, 139(3):1256-1261 (1986).

Diaz-Gómez et al., "Breast-feeding and growth factors in preterm newborn infants," *Journal of Pediatric Gastroenterology & Nutrition*, 24: 322-327 (1997).

Frystyk et al., "The relationship between the circulating IGF system and the presence of retinopathy in Type 1 diabetic patients," *Diabet. Med.*, 20(4): 269-276 (2003).

Gunn et al., "Growth hormone increases breast milk volumes in mothers of preterm infant," *Pediatrics*, 98: 279-282 (1996).

Hellstrom et al., "Low IGF-I suppresses VEGF-survival signaling in retinal endothelial cells: Direct correlation with clinical retinopathy of prematurity," *Proc Natl Acad Sci USA.*, 98(10):5804-5808 (2001).

Hellström et al., "Postnatal Serum Insulin-Like Growth Factor I Deficiency is Associated With Retinopathy of Prematurity and Other Complications of Premature Birth," *Pediatrics*, 112(5): 1016-1020 (2003).

Langford et al, "Maternal and fetal insulin-like growth factors and their binding proteins in the second and third trimesters of human pregnancy," *Hum Reprod.*, 13(5): 1389-1393 (1998).

Lofqvist et al., "IGFBP3 suppresses retinopathy through suppression of oxygen-induced vessel loss and promotion of vascular regrowth," *Proc Natl Acad Sci USA.*, 104(25): 10589-10594 (2007).

Löfqvist et al., "A Pharmacokinetic and Dosing Study of Intravenous Insulin-Like Growth Factor-I and IGF-Binding Protein-3 Complex to Preterm Infants," *Pediatr Res.*, 65(5): 574-579 (2009).

Mayo Clinic staff, "Premature birth," Website downloaded on Oct. 20, 2012 from mayoclinic.com/health/premature-birth/DS00137; 13 pages total.

Ning et al., "Diminished growth and enhanced glucose metabolism in triple knockout mice containing mutations of insulin-like growth factor binding protein-3, -4, and -5," *Mol. Endocrinol.*, 20(9): 2173-2186 (2006).

Patel et al., "The Contributions of Plasma IGF-I, IGFBP-3 and Leptin to Growth in Extremely Premature Infants During the First Two Years," *Pediatric Research*, 61(1): 99-104 (2007).

(Continued)

*Primary Examiner* — Christina Borgeest

(74) *Attorney, Agent, or Firm* — Finnegan, Henderson, Farabow, Garrett & Dunner, LLP

(57) ABSTRACT

The present invention relates to a composition comprising Insulin Growth Factor I (IGF-I) or an analog thereof in combination with Insulin Growth Factor Binding Protein (IGFBP) or an analog thereof, said combination having a molar ratio of IGF-I to IGFBP 5 being lower than equimolar, preferably in the range from 1:20 to 1:3.33, for use in the treatment of a patient suffering from complications of preterm birth, very preterm birth and/or extremely preterm birth, as well as a method for treating a patient suffering from complications of preterm birth, very preterm birth and/or extremely preterm birth.

9 Claims, 9 Drawing Sheets

(56) References Cited

OTHER PUBLICATIONS

Smith et al., "Use of Insulin-Like Growth Factor I (IGF-I) and IGF-Binding Protein Measurements to Monitor Feeding of Premature Infants," *Journal of Clinical Endocrinology and Metabolism*; 82: 3982-3988 (1997).

Smith et al., "Regulation of vascular endothelial growth factor-dependent retinal neovascularization by insulin-like growth factor-1 receptor," *Nature Medicine*, 5(12): 1390-1395 (1999).

Sommer et al., "Molecular genetics and actions of recombinant insulin-like growth factor binding protein-3," in Modern concepts of insulin-like growth factors (E. M. Spencer, ed., Elsevier, New York, 1991), pp. 715-728.

International Search Report from PCT/SE2008/050441, dated Jul. 11, 2008 (6 pages).

International Preliminary Report on Patentability and Written Opinion for PCT/SE2008/050441 issued Oct. 20, 2009 (12 pages).

Extended European Search Report for European Patent Application No. 08779242.0 mailed Dec. 19, 2012, (7 pages).

Restriction Requirement mailed Jul. 20, 2012, in U.S. Appl. No. 12/596,572.

Office Action mailed Nov. 2, 2012, in U.S. Appl. No. 12/596,572.

Notice of Allowance and Fee(s) Due mailed Apr. 26, 2013, in U.S. Appl. No. 12/596,572.

Corrected Notice of Allowability mailed May 21, 2013, in U.S. Appl. No. 12/596,572.

Office Action mailed Sep. 11, 2014, in U.S. Appl. No. 13/949,750.

Brown, D.R. et al. (1990) "Retinopathy of Prematurity: The Relationship With Intraventricular Hemorrhage and Bronchopulmonary Dysplasia" *Journal of Pediatric Ophthalmology & Strabismus*, 27(5):268-271.

Gien, J. and J.P. Kinsella (2011) "Pathogenesis and treatment of bronchopulmonary dysplasia" *Curr. Opin. Pediatr.*, 23(3):305-313. NIH Public Access Author Manuscript, doi: 10.1097/MOP. 0b013e328346577f; available in PMC Sep. 9, 2013 (18 pages).

Löfqvist, C. et al. (2012) "Low postnatal serum IGF-I levels are associated with bronchopulmonary dysplasia (BPD)" *Acta Paediatrica*, 101:1211-1216.

O'Keefe, M. et al. (2001) "Ocular significance of Intraventricular haemorrhage in premature infants" *Br. J. Ophthalmol.*, 85:357-359.

Phillips, J. et al. (1997) "Ocular morbidity in very low birth-weight infants with intraventricular hemorrhage" *Am. J. Ophthalmol.*, 123(2):218-223.

Procianoy, R.S. et al. (1981) "An association between retinopathy of prematurity and intraventricular hemorrhage in very low birth weight infants" *Acta. Paediatr. Scand.*, 70(4):473-477.

\* cited by examiner

METHODS FOR TREATMENT OF COMPLICATIONS OF PREMATURITY COMPRISING ADMINISTRATION OF IGF-I AND IGFBP-3

CROSS-REFERENCE TO RELATED APPLICATIONS

This application is a continuation of U.S. patent application Ser. No. 13/949,750, filed Jul. 24, 2013, which is a divisional of U.S. patent application Ser. No. 12/596,572, now U.S. Pat. No. 8,518,877 B2, whose 35 U.S.C. §371(c) date is Apr. 12, 2010, which is a National Stage application under 35 U.S.C. §371 of International Application No. PCT/SE2008/050441, filed Apr. 18, 2008, which claims the benefit of priority of U.S. Provisional Application No. 60/923,963, filed Apr. 18, 2007, all of which are incorporated herein by reference in their entirety.

DESCRIPTION

Technical Field

The present invention relates to a method for preventing the risk of developing complications of premature birth and low birth-weight, and particularly complications relating to low serum levels of circulating IGF-I and/or IGFBP-3.

BACKGROUND OF THE INVENTION

Of an estimated 4.3 million live births in the United States each year, approximately 87 000 (about 2.1%) occur very prematurely, defined as gestational age less than 32 weeks. In Europe it is estimated that the incidence of preterm birth less than 32 weeks of gestation is 1.2% in 10 000 inhabitants. Thus with 450 million inhabitants in EU25 the incidence of preterm births less 32 weeks of gestation is expected to be 54 000 infants per year. Preterm labor and its complications are major perinatal public health issues in developed societies today. Infants with low birth-weight or infants born prematurely miss part or all of the critical period of in utero growth. They account for half of all infant deaths and three-quarters of long-term morbidity. They impose a heavy burden on the national economy, because of the high costs of special care in both the neonatal period and over the life-span of survivors. Many survivors also have diminished quality of life because of physical damage resulting directly from prematurity.

The length of a normal pregnancy or gestation is considered to be 40 weeks (280 days) from the date of conception. Infants born before 37 weeks of gestation are considered premature and may be at risk for complications. Infants born before 32 completed weeks of gestation are considered very preterm and infants born before 28 completed weeks of gestation are considered born extremely preterm. Advances in medical technology have made it possible for infants born as young as 23 weeks gestational age (17 weeks premature) to survive. Infants born prematurely are at higher risk for death or serious complications due to their low birth weight and the immaturity of their body systems. Low birth weight, defined by a cut-off of 2500 g, serves as a marker for high risk newborns, as it is correlated with prenatal risk factors, intrapartum complications and neonatal disease, and is composed largely of preterm births. Studies on very low birth weight, defined as less than 1500 g or less than 1000 g cut-offs that identify infants at highest risk, those with high rates of severe respiratory and neurological complications associated with extreme prematurity.

The lungs, digestive system, and nervous system (including the brain) are underdeveloped in premature babies, and are particularly vulnerable to complications. The most prevalent medical problems encountered in preterm infants are developmental delay, mental retardation, bronchopulmonary dysplasia, intraventricular hemorrhage and retinopathy of prematurity. When preterm children are deprived of their natural environment they lose important factors normally found in utero, such as proteins, growth factors and cytokines. It has been demonstrated that insulin-like growth factor 1 (IGF-I) is one such factor, but it is likely there are others.

Insulin growth factor I (IGF-I) is a well-known regulator of postnatal growth and metabolism. It has a molecular weight of approximately 7.5 kilo Daltons (kDa). IGF-I has been implicated in the actions of various other growth factors, since treatment of cells with such growth factors leads to increased production of IGF-I. However, its role in prenatal growth and development has only recently been recognized. Experimental data obtained in IGF-I$^{-/-}$ mice suggest that IGF-I play an important role in the third trimester of embryonic growth and development of several tissues. In support of the IGF-I$^{-/-}$ data in mice, a patient homozygous for a gene defect in the IGF-I gene was shown to display impaired prenatal growth and development of the central nervous system.

IGF-I has insulin-like activities and is mitogenic (stimulate cell division) and/or is trophic (promote recovery/survival) for cells in neural, muscular, reproductive, skeletal and other tissues. Unlike most growth factors, IGF is present in substantial quantity in the circulation, but only a very small fraction of this IGF is free in the circulation or in other body fluids. Most circulating IGF is bound to the IGF-binding protein IGFBP-3. IGF-I may be measured in blood serum to diagnose abnormal growth-related conditions, e.g., pituitary gigantism, acromegaly, dwarfism, various growth hormone deficiencies, and the like. Although IGF-I is produced in many tissues, most circulating IGF-I is believed to be synthesized in the liver. In human fetal serum, IGF-I levels are relatively low and are positively correlated with gestational age and birth weight. Almost all IGF circulates in a non-covalently associated ternary complex composed of IGF-I, IGFBP-3, and a larger protein subunit termed the acid labile subunit (ALS). The IGF-I/IGFBP-3/ALS ternary complex is composed of equimolar amounts of each of the three components. ALS has no direct IGF binding activity and appears to bind only to the IGF-I/IGFBP-3 binary complex. The IGF-I/IGFBP-3/ALS ternary complex has a molecular weight of approximately 150 kDa. This ternary complex is thought to function in the circulation "as a reservoir and a buffer for IGF-I preventing rapid changes in the concentration of free IGF". It has been shown that excessive free IGF-I can down regulate the bioactivity of IGFBPs; thus, reduced IGFBP activity could also contribute to the lack of effect of high-dose IGF-I. Earlier pharmacokinetic studies in healthy children and adults have found half-life of the IGF-I/IGFBPs complex to be approximately 12 to 15 hours in plasma. IGFBP-3 is the most abundant IGF binding protein in the circulation, but at least five other distinct IGF binding proteins (IGFBPs) have been identified in various tissues and body fluids. Although these proteins bind IGFs, they each originate from separate genes and have unique amino acid sequences. Thus, the binding proteins are not merely analogs or derivatives of a common precursor. Unlike IGFBP-3, the other IGFBPs in the circulation are not saturated with IGFs. Moreover, none of the IGFBPs other than IGFBP-3 can form the 150 kDa ternary complex. The IGF-I/IGFBP-3 ratio in plasma has been used as an estimate of the availability of non protein-bound IGF-I, with an increased ratio suggesting an increased availability of free bio-active IGF-I. A higher IGF-I/IGFBP-3 ratio during the first postnatal month has been associated with higher growth velocity in moderately preterm, as compared to term infants. However conclusions from measuring the IGF-I and IGFBP-3 during the first postnatal month in infant born very and extremely preterm showed no difference in the IGF-I/IGFBP-3 ratio between healthy infants with morbidity (i.e. ROP).

IGF-I and IGFBP-3 may be purified from natural sources or produced by recombinant means. For instance, purification of IGF-I from human serum is well known in the art. Production of IGF-I by recombinant processes is shown in EP 0 128 733, published in December of 1984. IGFBP-3 may be purified from natural sources using a process such as that shown in Baxter et al. (1986, Biochem. Biophys. Res. Comm.

139:1256-1261). Alternatively, IGFBP-3 may be synthesized recombinantly as discussed in Sommer et al., pp. 715-728, MODERN CONCEPTS OF INSULIN-LIKE GROWTH FACTORS (E. M. Spencer, ed., Elsevier, New York, 1991). Recombinant IGFBP-3 binds IGF-I in a 1:1 molar ratio.

During fetal life these elements are introduced through placental absorption or ingestion from amniotic fluid (AF). Deprivation of such factors is likely to cause inhibition or improper stimulation of important pathways, which in the case of the eye may cause abnormal retinal vascular growth, the hallmark of retinopathy of prematurity (ROP). Understanding which factors are lost with preterm birth and evaluating their impact on the development of ROP will also have much greater implications for the growth and development of other organ systems (brain, lungs, gut, and bones). Replacing lost factors is likely to improve overall development. Therefore, research in this field is of great importance for the understanding of normal development of immature infants and for the prevention of many complications of preterm birth.

ROP is a major cause of blindness in children in the developed and developing world, despite current treatment of late-stage ROP. As developing countries provide more neonatal and maternal intensive care, the incidence of ROP is increasing. Although ablation treatment, such as laser photocoagulation or cryotherapy, of the retina reduces the incidence of blindness by 25% in those with late-stage disease, the visual outcome after treatment is often poor. Preventive therapy for ROP would clearly be preferable.

Retinal blood vessel development begins during the fourth month of gestation and is not completed until term. Therefore, infants born prematurely have incompletely vascularized retinas, with a peripheral a vascular zone, the area of which depends on the gestational age. With maturation of the infant, the resulting non-vascularized retina becomes increasingly metabolically active and hypoxic. The hypoxia-induced retinal neovascularization (NV) phase of ROP is similar to other proliferative retinopathies, such as diabetic retinopathy.

In the early 1950's studies in patients with proliferative diabetic retinopathy demonstrated that pituitary ablation resulted in total remission of the retinopathy indicating that growth hormone (GH) or some factor in the GH-axis played an important role for the development of retinopathy. GH was shown to be critical for retinopathy in a mouse model. In addition, experimental studies in a ROP mouse model demonstrated that an IGF-I receptor antagonist was found to suppress retinal neovascularization. IGF-I regulates retinal NV, at least in part, through control of vascular endothelial growth factor (VEGF) activation of p44/42 MAPK (a kinase inhibitor), establishing a hierarchical relationship between IGF-I and VEGF receptors. These studies establish a critical role for IGF-I in angiogenesis. IGF-I acts permissively to allow maximum VEGF stimulation of new vessel growth. Low levels of IGF-I inhibit vessel growth despite the presence of VEGF. Therefore, IGF-I is likely to be one of the non-hypoxia-regulating factors critical to the development of ROP (L. E. Smith, W. Shen, C. Perruzzi et al., Regulation of vascular endothelial growth factor-dependent retinal neovascularization by insulin-like growth factor-1 receptor. *Nat Med* 5 (1999), pp. 1390-1395).

Similar to the role of VEGF, it has been shown that IGF-I is critical for the normal development of the retinal vessels (Hellström, C. Perruzzi, M. Ju et al., Low IGF-I suppresses VEGF-survival signaling in retinal endothelial cells: direct correlation with clinical retinopathy of prematurity. *Proc Natl Acad Sci USA*. 98 (2001), pp. 5804-5808). IGF-I levels fall below in utero levels after birth, partly due to the loss of IGF-I provided by the placenta and the amniotic fluid. It has been hypothesized that IGF-I is critical to normal retinal vascular development, and that a lack of IGF-I in the early neonatal period is associated with lack of vascular growth and with subsequent proliferative ROP. In IGF-I knockout mice (IGF-I–/–), normal retinal vascular development was examined to determine whether IGF-I is critical to normal blood vessel growth. Retinal blood vessels grow more slowly in IGF-I–/– mice than in those of normal mice, a pattern very similar to that seen in premature babies with ROP. These observations were confirmed in patients with ROP (Hellström, C. Perruzzi, M. Ju et al., Low IGF-I suppresses VEGF-survival signaling in retinal endothelial cells: direct correlation with clinical retinopathy of prematurity. *Proc Natl Acad Sci USA*. 98 (2001), pp. 5804-5808 and Hellström A, Engstrom E, Hard A-L, et al. Postnatal serum IGF-I deficiency is associated with retinopathy of prematurity and other complications of premature birth pediatrics, *Pediatrics* 2003; 112: 1016-1020).

In a previous patent application, US 2004/0053838, generally related to determining the risk of developing complications of premature birth and low birth weight and to methods for treatment of such complications, these complications are associated with low levels of IGF-I. The therapeutic approach suggested treatment of complications of prematurity by administration of IGF-I to a patient, to elevate the patient's serum levels of IGF-I to an in utero baseline level. According to one of the methods for treatment in accordance with said invention, IGF-I can be administered in a composition comprising IGF-I in combination with an additional protein that is capable of binding IGF-1 and propose such binding protein to be IGF-I binding protein 3 (IGFBP-3). It is further suggested that a composition comprising equimolar amounts of IGF-I and IGFBP-3 may be used.

In U.S. Pat. No. 5,187,151 (Genentech) co-administration of IGF-I and IGFBP, is suggested in general, in a molar ratio of IGFBP-3 to IGF-I of about 0.5:1 to 3:1 (or as the molar ratio is expressed as IGF-I/IGFBP-3 throughout the present application corresponding molar ratios disclosed in U.S. Pat. No. 5,187,151 would be 1:0.5 to 1:3 when compared to the molar ratios claimed in the present invention) by subcutaneous bolus injection. They state that the mixture to be used in therapy will be formulated and dosed in a fashion consistent with good medical practice, taking into account the clinical condition of the individual patient (including any perceived or anticipated side or reduced anabolic effects using IGF-I alone, the particular growth defect or catabolic state to be corrected, the particular IGFBP being utilized, the site of delivery of the mixture and other factors known to the practitioners. Further methods for manufacture of IGF-I and IGFBP compositions with varying molar ratios are known from prior art. However, the beneficial effect of administration of a combination of the two components in a specific ratio range is not disclosed in the literature. In particular, there is to the best of our knowledge no teaching or indication in the prior art what IGF-I based method would be expected to provide the most efficient way of treatment of premature children running a clear risk of acquiring a handicap for the rest of their life.

Despite the ever-increasing advances in the understanding of complications of prematurity, there are no presently available effective treatments or methods of determining the risk of developing these life-threatening conditions, as premature death is still the norm.

SUMMARY OF THE INVENTION

It is the object of the present invention to provide a new composition comprising Insulin Growth Factor I (IGF-I) or an analog thereof in combination with Insulin Growth Factor Binding Protein (IGFBP) or an analog thereof to be used in the treatment of a patient suffering from complications of preterm birth, very preterm birth and/or extremely preterm birth.

DETAILED DESCRIPTION OF THE PRESENT INVENTION

In particular the present invention relates to a composition comprising Insulin-like Growth Factor I (IGF-I) or an analog thereof in combination with Insulin-like Growth Factor Binding Protein (IGFBP) or an analog thereof, said combination having a molar ratio of IGF-I to IGFBP being lower than equimolar, preferably in the range from 1:20 to 1:3.33, for use in the treatment of a patient suffering from complications of preterm birth, very preterm birth and/or extremely preterm birth.

In a preferred embodiment thereof, the molar ratio of IGF-I to IGFBP is in the range from 1:20 to 1:4, preferably from 1:15 to 1:5, more preferably from 1:12 to 1:8.

In a preferred embodiment thereof, the composition is continuously adjusted with regard to its content of IGFBP to achieve a serum concentration having a molar ratio corresponding to the patient's gestational age.

In a preferred embodiment thereof, the Insulin Growth Factor Binding Protein (IGFBP) is IGFBP-3 or an analog thereof.

In a preferred embodiment thereof, the dose range for IGF-I is from 5 to 450 μg/kg per 24 hours In a preferred embodiment thereof, the complications of preterm birth, very preterm birth and/or extremely preterm birth are conditions associated with low circulating levels of IGF-I and/or IGFBP-3.

In a preferred embodiment thereof, the complication of preterm birth, very preterm birth and/or extremely preterm birth is one from the group comprising developmental delay, mental retardation, bronchopulmonary dysplasia, intraventricular hemorrhage and retinopathy of prematurity (ROP).

In a preferred embodiment thereof, the complication of preterm birth is retinopathy of prematurity (ROP).

In a preferred embodiment thereof, said complication of preterm birth, very preterm birth and/or extremely preterm birth is indicated by the patient having a serum level of IGF-I and/or IGFBP-3 below the norm for in utero levels corresponding to normal levels for the patient's gestational age.

In a preferred embodiment thereof, the use includes intravenous (IV), intramuscular (IM), subcutaneous (SC), intraperitoneal (IP), intranasal, microdialysis and inhalation treatment In a preferred embodiment thereof, the use includes subcutaneous, intravenous or oral treatment.

In a preferred embodiment thereof, the use includes intravenous treatment.

In a preferred embodiment thereof, the treatment is initiated not later than five days post-birth, preferably not later than four days post-birth, more preferably not later than three days post-birth, most preferably not later than two days post-birth.

In a preferred embodiment thereof, the IGF-I analog is rhIGF-I and IGFBP-3 analog is rhIGFBP-3.

A further aspect of the present invention relates to a method for preventing a patient from developing a complication of preterm birth comprising administering to a patient having a serum level of IGF-I and/or IGFBP-3 below the norm for in utero, an effective amount of IGF-1 or an analog thereof in combination with IGF-I binding protein 3 (IGFBP-3) or an analog thereof, wherein the molar ratio of IGF-I to IGFBP being lower than equimolar, preferably in the range from 1:20 to 1:3.33, to elevate the patient's IGF-1 and/or IGFBP-3 serum levels to in utero levels corresponding to normal levels for the patient's gestational age.

In a preferred embodiment thereof, the molar ratio of IGF-I to IGFBP is in the range from 1:20 to 1:4, preferably from 1:15 to 1:5, more preferably from 1:12 to 1:8.

In a preferred embodiment thereof, the composition is continuously adjusted with regard to its content of IGFBP to achieve a serum concentration having a molar ratio corresponding to the patient's gestational age.

In a preferred embodiment thereof, the Insulin Growth Factor Binding Protein (IGFBP) is IGFBP-3 or an analog thereof.

In a preferred embodiment thereof, the dose range for IGF-I is from 5 to 450 μg/kg per 24 hours In a preferred embodiment thereof, the complications of preterm birth, very preterm birth and/or extremely preterm birth are conditions associated with low circulating levels of IGF-I and/or IGFBP-3.

In a preferred embodiment thereof, the complication of preterm birth, very preterm birth and/or extremely preterm birth is one from the group comprising developmental delay, mental retardation, bronchopulmonary dysplasia, intraventricular hemorrhage and retinopathy of prematurity (ROP).

In a preferred embodiment thereof, the complication of preterm birth is retinopathy of prematurity (ROP).

In a preferred embodiment thereof, said complication of preterm birth, very preterm birth and/or extremely preterm birth is indicated by the patient having a serum level of IGF-I and/or IGFBP-3 below the norm for in utero levels corresponding to normal levels for the patient's gestational age.

In a preferred embodiment thereof, the use includes intravenous (IV), intramuscular (IM), subcutaneous (SC), intraperitoneal (IP), intranasal, microdialysis and inhalation treatment In a preferred embodiment thereof, the use includes subcutaneous, intravenous or oral treatment.

In a preferred embodiment thereof, the use includes intravenous treatment.

In a preferred embodiment thereof, the treatment is initiated not later than five days post-birth, preferably not later than four days post-birth, more preferably not later than three days post-birth, most preferably not later than two days post-birth.

In a preferred embodiment thereof, the IGF-I analog is rhIGF-I and IGFBP-3 analog is rhIGFBP-3.

DEFINITIONS

"Preterm" or "preterm birth" or "prematurity" refers to birth of a patient prior to 40 weeks of gestation or weighing 10% less than the average for the patient's gestational age.

"Very preterm birth" refers to infants born before 32 completed weeks of gestation.

"Extremely preterm birth" refers to infants born before 28 completed weeks of gestation.

"IGF-I" refers to insulin-like growth factor I from any species, including bovine, ovine, porcine and human, in native-sequence or variant form, including but not limited to naturally-occurring allelic variants. IGF-I may be from any source, whether natural, synthetic or recombinant, provided that it will bind IGFBP-3 at the appropriate site. Preferred herein is human IGF-I. IGF-I can be produced recombinantly, for example, as described in PCT publication WO 95/04076.

An "IGFBP" or an "IGF binding protein" refers to a protein or polypeptide from the insulin-like growth factor binding protein family and normally associated with or bound or complexed to IGF-I whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs.

"IGFBP-3" refers to insulin-like growth factor binding protein 3. IGFBP-3 is a member of the insulin-like growth factor binding protein family. IGFBP-3 may be from any species, including bovine, ovine, porcine and human, in native-sequence or variant form, including but not limited to naturally-occurring allelic variants. IGFBP-3 can form a binary complex with IGF-I, and a ternary complex with IGF and the acid labile subunit (ALS). IGFBP-3 may be from any source, whether natural, synthetic or recombinant, provided that it will bind IGF-I and ALS at the appropriate sites. IGFBP-3 can be produced recombinantly, as described in PCT publication WO 95/04076.

"IGF-I/IGFBP-3 ratio" refers to the ratio of IGF-I to IGFBP-3, and is defined as either IGF-I divided by IGFBP-3 in absolute values and presented as percent or as the IGF-I/IGFBP-3 molar ratio. For molar comparisons between IGF-I and IGFBP-3, the following molecular masses were used in the calculation: IGF-I, 7.5 kDa (i.e. 7649 Da); and IGFBP-3, 28.7 kDa (i.e 28732 Da). The molar ratio of IGF-I to IGFBP-3 is calculated as an indicator of the bioactive IGF-I using the following equivalents for conversion: 1 ng/mL IGF-I=0.130 nmol/L IGF-I; 1 ng/mL IGFBP-3=0.036 nmol/L IGFBP-3.

A "therapeutic composition," as used herein, is defined as comprising IGF-I, an analog thereof, or IGF-I in combination with its binding protein, IGFBP-3 (IGF-I/IGFBP-3 complex). The therapeutic composition may also contain other substances such as water, minerals, carriers such as proteins, and other excipients known to one skilled in the art.

"Analogs" of IGF-1 are compounds having the same therapeutic effect as IGF-I in humans or animals. These can be naturally occurring analogs of IGF-I (e.g., truncated IGF-I) or any of the known synthetic analogs of IGF-I. See, for example, U.S. Pat. Nos. 6,251,865 and 5,473,054.

BRIEF DESCRIPTION OF THE DRAWINGS (OPTIONAL)

In the following the invention will be described in a non-limiting way and in more detail with reference to exemplary embodiments illustrated in the enclosed drawings, in which:

FIG. 1 shows the pharmacokinetic serum ratio of IGF-I/IGFBP3 in 5 children after the intravenous infusion of rhIGF-I/rhIGFBP-3 in an equimolar combination administered over 3 hours at 5 and 60 μg/kg/dose (equivalent to 1 and 13 μg/kg/rhIGF-I)

DETAILED DESCRIPTION OF PREFERRED EMBODIMENTS

Figure 1:
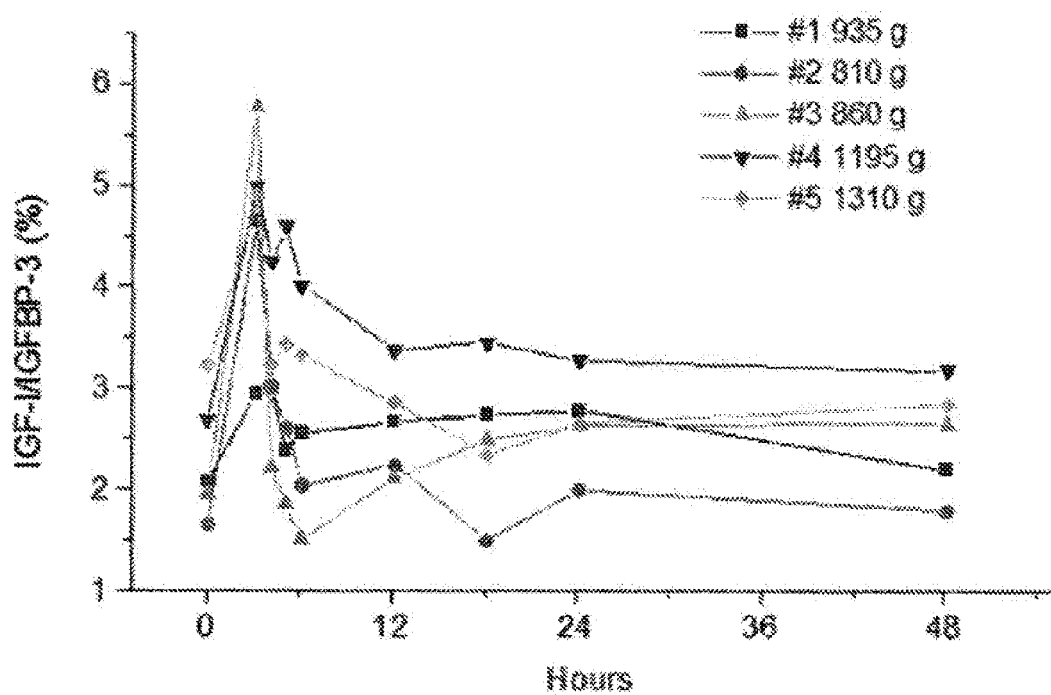

In US 2004/0053838 it is demonstrated that IGF-I is necessary for vascular growth and rationalize the disease process of ROP, which begins with cessation of the growth of retinal vessels after premature birth. A key difference between vascular growth in utero and after birth is that the concentration of IGF-I falls in premature infants after birth. The disclosure in 2004/0053838 suggest that if the level of IGF-I increases quickly in premature infants after delivery, allowing normal vascular development, ROP does not occur.

VEGF has been shown to play a significant role in the development of blood vessels but is insufficient in the presence of low IGF-I levels to allow blood vessel growth. VEGF is produced in the increasingly hypoxic avascular retina as metabolic demands increase with development and VEGF levels rise in the vitreous. When IGF-I rises more quickly after birth as occurs in the non-ROP infants, VEGF does not accumulate since vascular growth can occur which provides oxygen to the maturing retina and controls VEGF production. When the concentration of IGF-I is low for an extended period, vessels cease to grow, the maturing avascular retina becomes hypoxic and VEGF accumulates in the vitreous. As the concentration of IGF-I rises to a threshold level when high levels of VEGF are present, a rapid growth of new blood vessels (retinal neovascularization) is triggered. This rapid vascular growth is likely based on increased survival and proliferation of vascular endothelial cells since IGF-I and VEGF are complementary for endothelial cell function through the MAPK and AKT signal transduction pathways. In particular, the data indicates that IGF-I (and perhaps other cytokines) is necessary at minimal levels to promote maximum function of VEGF.

The disclosure in US 2004/0053838 shows that IGF-I levels can be used to predict which babies will develop ROP. The differences in pattern of IGF-I levels between infants that do and do not develop ROP suggest that increasing serum concentrations of IGF-I early after birth may prevent this disease. The relative risk for ROP and other morbidity was increased 5.7-fold (95% confidence interval 2.2-14.6) if IGF-I was ≤30 µg/L at 33 weeks post-menstrual age. After adjustment for post-menstrual age, each increase of 5 µg/L mean IGF-I during post-menstrual age 31-35 weeks decreased the risk of ROP by 59%. The median level of IGF-I at 31-35 weeks of gestation was 26 µg/L (range 17-49) for infants with ROP and other morbidity (n=19), compared to 38 µg/L (range 20-59) in the group without postnatal morbidity (n=29), p<0.0001.

After premature birth potential sources of IGF-I are lost, including ingestion of amniotic fluid, which contains high levels of IGF-I. The concentration of IGF-I may be increased to the levels found in infants without ROP through increased caloric intake, oral ingestion of IGF-I to mimic ingestion of amniotic fluid, or an intravenous supply to raise IGF-I to a more normal level. Since ROP is correlated with other developmental problems, increasing IGF-I levels to the level of infants without ROP may also improve neurological development.

Both IGF-I and VEGF are also important factors in the second or neovascular phase of ROP. It is suggested that early intervention to increase the concentration of IGF-I would allow normal vascular growth and prevent the development of the second potentially destructive phase of ROP, late intervention after accumulation of VEGF might trigger or exacerbate retinal neovascularization. According to one of the methods for treatment in accordance with the disclosure in US 2004/0053838, IGF-I can be administered in a composition comprising IGF-I in combination with an additional protein that is capable of binding IGF-I and propose such binding protein to be IGF-I binding protein 3 (IGFBP-3). It is further suggested that a composition comprising equimolar amounts of IGF-I and IGFBP-3 may be used.

In an initial study to determine IGF-I and IGFBP-3 pharmacokinetic profiles after the administration of intravenous infusion of recombinant (rh) IGF-I/rhIGFBP-3 to very low birth weight (VLBW) infants and to evaluate safety and tolerability a composition of equimolar amounts of IGF-I and IGFBP-3 (as suggested in US 2004/0053838) was used. This was an open label clinical study conducted in the Neonatal Ward at Queen Silvia Children's hospital in Gothenburg in 2007. Five patients (3 females) with mean (range) gestational age of 27 weeks (26 weeks+0 day to 29 weeks+1 day) and a birth weight of 1 022 grams (810 to 1310 grams) participated in the study. On the infants day 3 (chronological age) rhIGF-I/rhIGFBP-3 in an equimolar combination (that is equal amounts of rhIGF-I and rhIGFBP-3 as a complex) was administered as an intravenous infusion over 3 hours at 5 and 60 µg/kg/dose (equivalent to 1 and 13 µg/kg/rhIGF-I). The results can be seen in FIG. 1 which shows the influence of the administered rhIGF-I/rhIGFBP-3 complex on the serum IGF-I/IGFBP3 ratios for the children. Baseline IGF-I and IGFBP-3 levels at the start of infusion were 18.8 d 6.1 and 811.8±152.4 µg/L, respectively (that is a percentage ratio of 2.3%, which corresponds to a molar ratio of IGF-I to GFBP-3 of about 1:12). Immediately after stopping the study drug infusion, serum IGF-I and IGFBP-3 levels were 39.6±12.2 and 856.6±197.6 µg/L, respectively (that is a percentage ratio of 4.6% corresponding to a molar ratio of IGF-I to IGFBP-3 of about 1:6). It is also seen that the mean concentration of IGF-I was increased from the sight-threatening ROP low levels of ≤30 µg/L (mean of 18.8 µg/L in this study) to a level ≥35 µg/L (39.6 µg/L) which according to US 2004/0053838 indicates a non-ROP threatening condition. There were no acute adverse events reported, all blood glucose measurements and extensive safety measures were all normal. In conclusion: These data demonstrated that the rhIGF-I/rhIGFBP-3 complex was effective in increasing serum IGF-I levels from low levels into the normal range for very preterm infants and that administration of rhIGF-I/rhIGFBP-3 was safe and well tolerated.

However, while serum concentrations of IGF-I more than doubled following transfusion and thereby reached levels described as physiological in the fetus at similar gestational ages, it is evident from the serum ratio graphs in FIG. 1 that the same increase in serum concentrations of IGFBP-3 could not be achieved. The molar ratio of IGF-1 to IGFBP-3 in serum increased from 1:12 to 1:6 following the infusion. Another important finding from this study was that the half-life in preterm infants being around one hour differed significantly from what has been shown for children and adult. Therefore, one of the major conclusion from this study was that rIGF-I/IGFBP-3 complex needs to be given as a continuous infusion. Furthermore, with a higher relative increase in the serum concentrations of IGF-I as compared to IGFBP-3, resulting in a higher IGF-I/IGFBP-3 ratio in serum, it could be concluded that administration of an equimolar composition of IGF-I/IGFBP-3 might not be optimal in premature infants.

This influence on increasing the IGF-I level and consequently also the IGF-I/IGFBP-3 molar ratio raises concerns as in a clinical study of premature infants (discussed below) it was found that also increased levels of IGFBP-3 are associated with reduced risk of ROP Therefore in order to better define the role of IGFBP-3 in angiogenesis in vivo, the effect of IGFBP-3 on retinal vascular survival and vascular re-growth in a mouse model of oxygen-induced vessel loss and subsequent hypoxia-driven neovascularization was examined.

In this model exogenous delivery of IGFBP-3 as well as Igfbp3$^{-/-}$, Igfbp3$^{+/-}$ and Igfbp3$^{++}$ transgenic mice which have various levels of IGFBP-3 expression, were used to examine the effects of modulation of IGFBP-3 levels on retinopathy in vivo. It was found that increasing levels of IGFBP-3 are associated with increased vessel survival in hyperoxia-induced vascular loss and with increased vessel re-growth and repair during the hypoxic phase of oxygen-induced retinopathy resulting in decreased retinopathy with increasing levels of IGFBP-3 in the mouse model of ROP.

In the following examples the invention will be described in more detail. These examples are given to illustrate and further characterize the invention and should not be limiting to the present invention. The following materials and methods were used to carry out the methods of the invention:

Animals.

These studies adhered to the ARVO Statement for the Use of Animals in Ophthalmic and Vision Research (www.arvo.org/AboutARVO/animalst.asp). IGFBP-3, IGFBP-3$^{-/-}$, IGFBP-3$^{+/-}$, IGFBP-3$^{+/+}$ mice were as described in Ning, Y., Schuller, A. G., Bradshaw, S., Rotwein, P., Ludwig, T., Frystyk, J. & Pintar, J. E. (2006) *Mol Endocrinol* 20, 2173-86. and were characterized by expression of IGFBP-3 mRNA in tail samples with real time RT-PCR and confirmed by Southern blot analysis Quantitative Analysis of Gene Expression (Quantitative Real-Time RT-PCR).

PCR primers targeting IGFBP-3, and an unchanging control gene (cyclophilin), RNA were designed by using Primer Express software (Applied BioSystems, Foster City, Calif.). We used three methods to analyze primer and probe sequences for specificity of gene detection. First, only primer and probe sequences that specifically detect the sequence of choice, as determined by means of the NCBI Blast module, were used. Second, amplicons generated during the PCR reaction were analyzed using the first derivative primer melting curve software supplied by Applied BioSystems. This analysis determines the presence of amplicons on the basis of their specific melting point temperatures. Third, amplicons generated during the PCR reaction were gel purified and sequenced (Children's Hospital Core Sequencing Facility, Boston, Mass.) to confirm the selection of the desired sequence. Quantitative analysis of gene expression was generated using an ABI Prism 7700 Sequence Detection System (TaqMan) and the SYBR Green master mix kit (Qiagen). C57Bl/6 mice were analyzed at P8, P10, P12, P15, P17, P26 and P33 with and without exposure to 75% oxygen by real-time PCR for levels of IGFBP-3 mRNA.

Laser capture microdissection. Eyes embedded in OCT were sectioned at 8 μm in a cryostat, mounted on uncoated glass slides, and immediately stored at −80° C. Slides containing frozen sections were immediately fixed in 70% ethanol for 30 s and stained with hematoxylin (Meyers) and eosin, which as followed by 4 dehydration steps each in 70%, 95%, and 100% ethanol and a final 10 min dehydration step in xylene. Once they were air dried, the sections were microdissected for vessels and retinal neuron layers with a PixCell II LCM system (Arcturus Engineering, Mountain View, Calif.). Each population was estimated to be >95% homogeneous as determined by microscopic visualization of the captured cells. Material from each cell layer from more than four mice was combined, RNA isolated, converted to cDNA as described. Specific cDNA was quantified using quantitative real-time (qRT) PCR.

EXAMPLE 1

Serum IGF-I Levels are Unchanged from Wild Type in IGFBP-3 Null Mice

The following studies adhered to the ARVO Statement for the Use of Animals in Ophthalmic and Vision Research www.arvo.og/AboutARVO/animalst.asp). IGFBP-3, IGFBP-3$^{-/-}$, IGFBP-3$^{+/-}$, IGFBP-3$^{+/+}$ mice were as described in Ning, Y., Schuller, A. G., Bradshaw, S., Rotwein, P., Ludwig, T., Frystyk, J. & Pintar, J. E. (2006) *Mol Endocrinol* 20, 2173-86, and were characterized by expression of IGFBP-3 mRNA in tail samples with real time RT-PCR and confirmed by Southern blot analysis (data not shown).

Serum IGF-1 levels were measured on IGFBP-3$^{-/-}$ (n=8), and IGFBP-3$^{-/+}$ (n=11) and IGFBP-3+/+ (n=10) sibling mice using an IGFBP-blocked RIA with a large excess of IGF-II for determination of IGF-I (Mediagnost GmbH, Tübingen, Germany). The intraassay CVs for the IGF-I assay were 11.1, 7.2, and 7.4% at concentrations of 36, 204, and 545 μg/L, respectively, and the interassay CVs were 13.5, 8.8, and 9.9%. This assay can be used as heterologous assay for mouse utilizing Rat IGF-I in the standard curve.

The mean serum IGF-I level as measured at postnatal day 5 (P5) in IGFBP-3$^{-/-}$ (n=8), IGFBP-3$^{+/-}$ (n=11) and IGFBP-3$^{+/+}$ (n=10) sibling mice was 89±19, 88±8 and 95±25 μg/L respectively indicating that there was no significant difference in IGF-I in transgenic mice compared to controls. There was also no difference in weight between IGFBP3$^{-/-}$ mice and IGFBP3$^{+/+}$ mice during development.

EXAMPLE 2

IGFBP-3 Protects Against Oxygen-Induced Retinal Vessel Loss (P8)

To induce vessel loss, postnatal day 7 (P7) mice with their nursing mother were exposed to 75% oxygen for times ranging from 18 h to 5 days. After $O_2$ exposure, the mice were anesthetized with Avertin (Sigma) and sacrificed by intracardiac perfusion with 20 mg/ml of $2×10^6$ mol wt FITC-dextran in saline. The eyes were enucleated and fixed in 4% paraformaldehyde for 2 h at 4° C. The retinas were isolated and whole-mounted with glycerol-gelatin (Sigma) onto polylysin-coated slides with the photoreceptor side up. The retinas were examined with a fluorescence microscope (Olympus, Tokyo), digitized images using a three-charge-coupled device color video camera (DX-950P, Sony), and processed with NORTHERN ECLIPSE software (Empix Imaging, Toronto).

Figure 2:
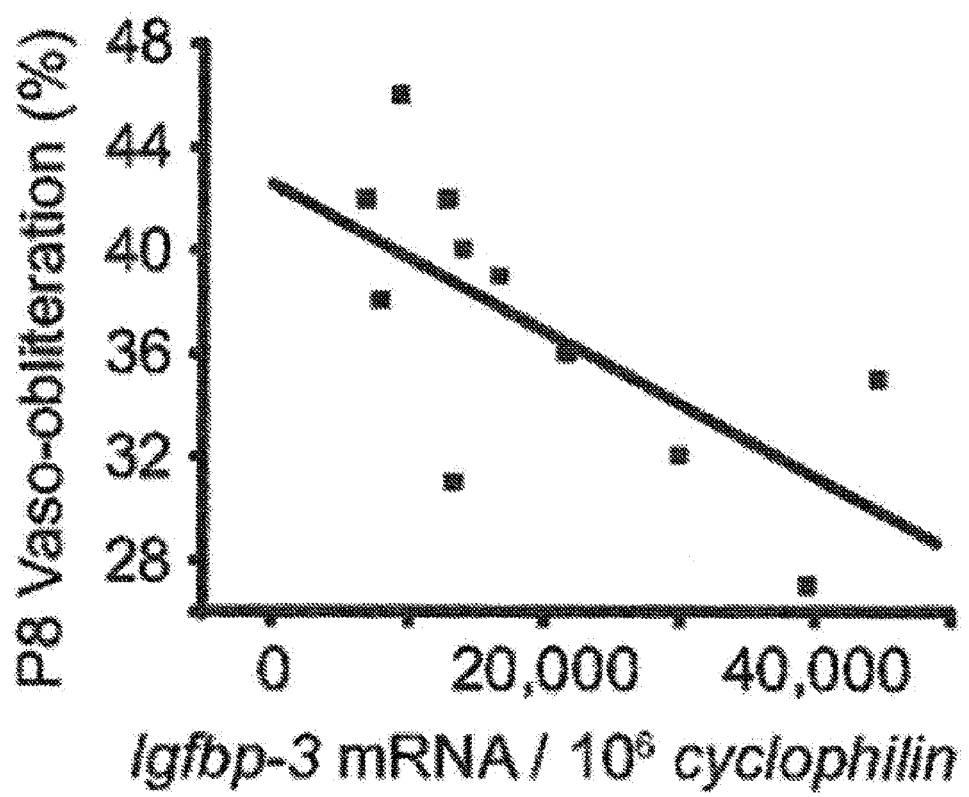
FIG. 2 shows that IGFBP-3 mRNA expression is associated with protection against oxygen-induced retinal vessel loss in a dose dependent manner.

To evaluate the effect of low IGFBP-3 on vessel survival in oxygen the degree of vessel loss in whole mounted retinas of IGFBP-3$^{+/+}$ or IGFBP-3$^{+/-}$ mice (n=22 eyes) was examined at P 8 after 17 hours of oxygen induction (n=11 mice; each data point is the mean of the right and the left eyes of one mouse). The degree of vessel loss was compared to IGFBP-3 mRNA expression in tail snips in heterozygote and wild type mice. From FIG. 2 it is seen that Igfbp3 mRNA expression is associated with protection against oxygen induced retinal vessel loss in a dose-dependent manner at P8 after 18 h of 75% oxygen in Igfbp3$^{+/-}$ mice, as there was a significant increase in vessel survival with increasing levels of IGFBP-3 mRNA expression (FIG. 2) (P5≤0.006, r=−0.70).

EXAMPLE 3

Low IGFBP-3 is Associated with Persistent Vaso-Obliteration at P17

Between P7 and P12 heterozygote IGFBP-3 mothers with pups were exposed to 75% oxygen, then removed to room air from P12-P17 and subsequently sacrificed. Retinas from IGFBP-3$^{-/-}$ (n=52 eyes) and IGFBP-3$^{+/+}$ mice (n=38 eyes) were isolated and whole mounted and area of vaso-obliteration evaluated.

Figure 3:
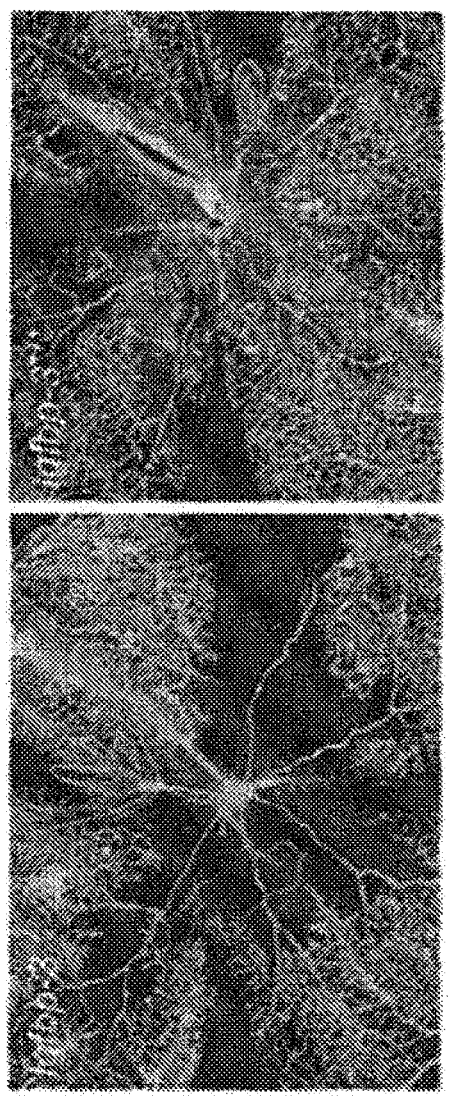
FIG. 3 shows that loss of IGFBP-3 decreases retinal vessel re-growth after oxygen induced loss.
Figure 3:
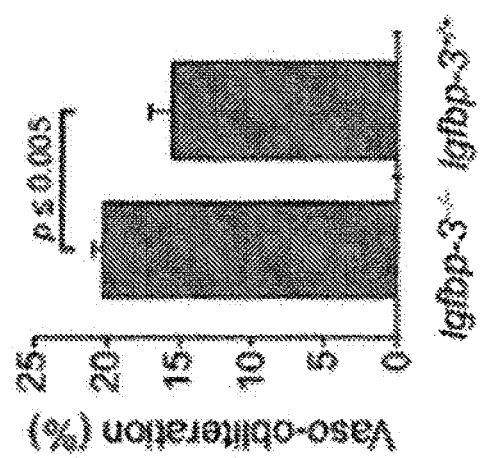

To evaluate the effect of IGFBP-3 on persistence of vessel loss the area of vaso-obliteration that persisted at P17 in whole mounted retinas of IGFBP-3$^{-/-}$ (n=52 eyes) and sibling IGFBP-3$^{+/+}$ (n=38 eyes) mice was examined after oxygen-induction of vessel loss (P7-P12) and vascular regrowth in room air P12-P17. In FIG. 3 it is seen that IGFBP-3 protection after oxygen-induced vessel loss persists as shown at P17 in WT (n=38 eyes) (center) compared to IGFBP-3$^{-/-}$ mice (n=52 eyes) (right). Fractional retinal area of vaso-obliteration in IGFBP3$^{-/-}$ mice was 20.2+/−0.1% (SEM) compared to wild type mice with an area of 15.1+/−0.5% (P≤0.005) (FIG. 3A). Representative retinal whole mounts shows less vessel loss in wild type than in IGFBP3$^{-/-}$ mice (FIG. 3B). There was a 31% increase in area of retinal vessel loss (P<0.005) in the IGFBP-3$^{-/-}$ mice compared to IGFBP-3$^{+/+}$ indicating persistence of vascular loss and/or lack of vessel re-growth with low IGFBP-3.

EXAMPLE 4

Exogenous IGFBP-3 Increases Vessel Re-Growth

Between P7 and P12, C57Bl/6 mice were exposed to 75% oxygen. After removal from oxygen at P12 mice were given 3 daily i.p. injections (P12-P14) with 60 μg of IGFBP-3 (n=16 eyes) or vehicle (n=14 eyes). The mice were sacrificed at P15 and retinas isolated and whole-mounted and area of vaso-obliteration evaluated for the effect of IGFBP-3 on re-growth of vessels.

Figure 4:
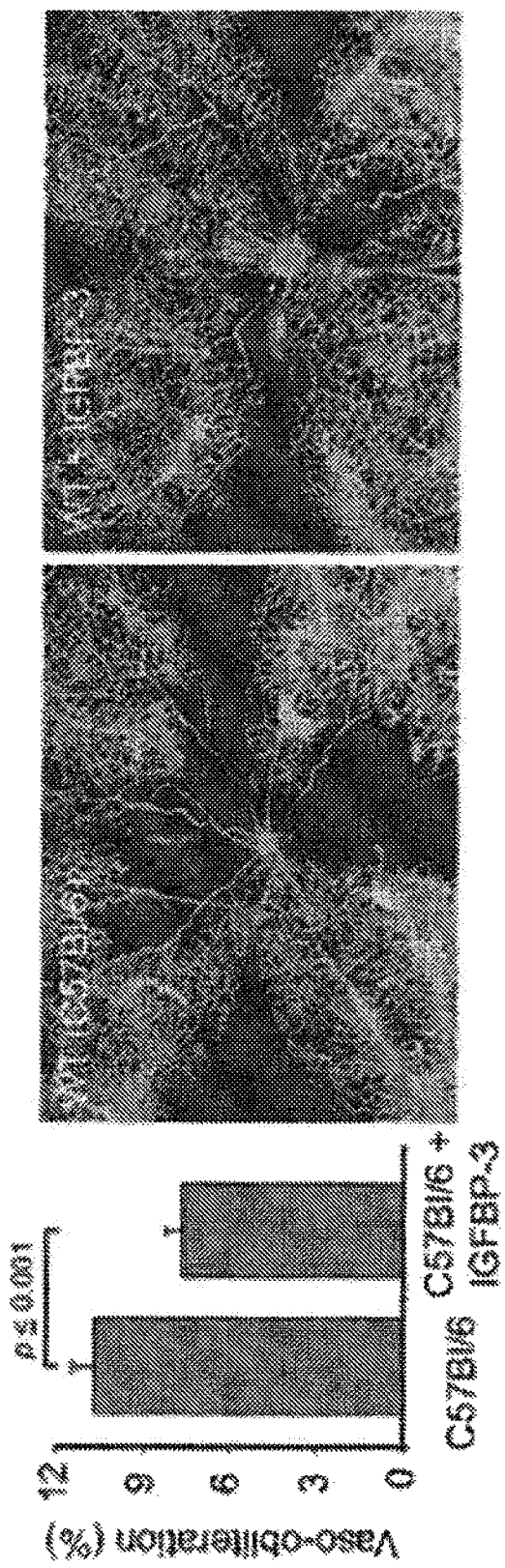
FIG. 4 shows that exogenous IGFBP-3 further increases vessel re-growth over baseline.

To evaluate the effect of elevated levels of serum IGFBP-3 on vessel re-growth after oxygen-induced vaso-obliteration, the vessel area in whole mounted retinas at P15 in C57Bl/6 mice given 3 daily injections of IGFBP-3 from P12-P14 after vessel loss induced by oxygen was examined. FIG. 4 center and right show that whole mounted retinas of C57Bl6 mice treated with saline after oxygen-induced vessel loss (center) have decreased vessel re-growth centrally than littermates treated with i.p. IGFBP-3 (right) from P12-P14. At P15 there was a 40% decrease in area of vessel loss in C57Bl/6 mice (n=8 mice) treated with IGFBP-3 compared to vehicle control treated mice (n=7) indicating increased vessel re-growth with increased IGFBP-3 (P≤0.001) (FIG. 4 left).

EXAMPLE 5

Increasing IGFBP-3 Expression is Associated with Decreasing Retinal Neovascularization in Mice Between P7 and P12 heterozygote IGFBP-3 mothers with pups were exposed to 75% oxygen, then removed to room air from P12-P17 and subsequently sacrificed. Retinas from IGFBP-3$^{-/+}$ and IGFBP-3$^{+/+}$ mice (n=9 mice, 18 eyes) were isolated and whole mounted and area of neovascularization evaluated and recorded as the mean of 2 retinas. IGFBP-3 mRNA levels were determined from tail snips as described.

Figure 5:
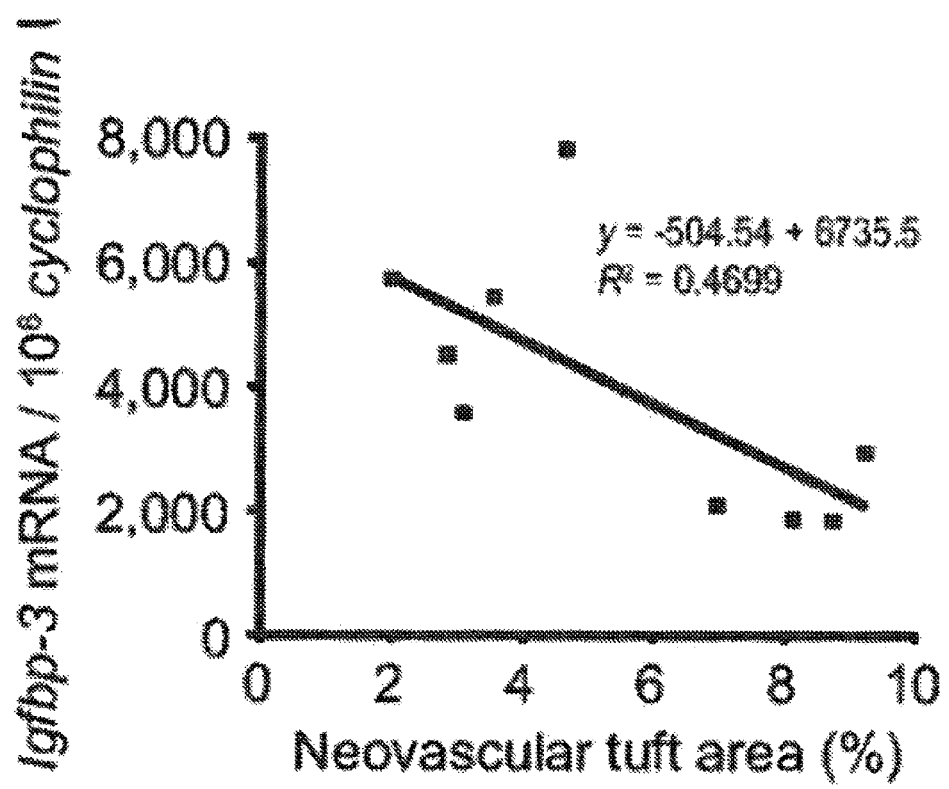
FIG. 5 shows that retinal neovascularization decreases with increasing IGFBP3.

To evaluate the association of IGFBP-3 mRNA with retinal neovascularization IGFBP-3−/+ and IGFBP-3+/+ (11 mice=22 eyes) sibling mice were evaluated for IGFBP-3 mRNA expression levels in tail snips and the degree of retinal neovascularization evaluated at P17 in whole mounted retinas. There was decreased retinal neovascularization with increasing IGFBP-3 mRNA expression. IGFBP-3 mRNA expression is associated with protection in a dose-dependent manner against retinal neovascularization in the ROP mouse model at P17 in IGFBP3$^{+/-}$ mice (FIG. 5).

EXAMPLE 6

Retinal IGFBP-3 mRNA Increases with Hypoxia

PCR primers targeting IGFBP-3, and an unchanging control gene (cyclophilin), RNA were designed by using Primer Express software (Applied BioSystems, Foster City, Calif.). We used three methods to analyze primer and probe sequences for specificity of gene detection. First, only primer and probe sequences that specifically detect the sequence of choice, as determined by means of the NCBI Blast module, were used. Second, amplicons generated during the PCR reaction were analyzed using the first derivative primer melting curve software supplied by Applied BioSystems. This analysis determines the presence of amplicons on the basis of their specific melting point temperatures. Third, amplicons generated during the PCR reaction were gel purified and sequenced (Children's Hospital Core Sequencing Facility, Boston, Mass.) to confirm the selection of the desired sequence. Quantitative analysis of gene expression was generated using an AIM Prism 7700 Sequence Detection System (TaqMan) and the SYBR Green master mix kit (Qiagen). C57Bl/6 mice were analyzed at P8, P10, P12, P15, P17, P26 and P33 with and without exposure to 75% oxygen by real-time PCR for levels of IGFBP-3 mRNA.

Figure 6:
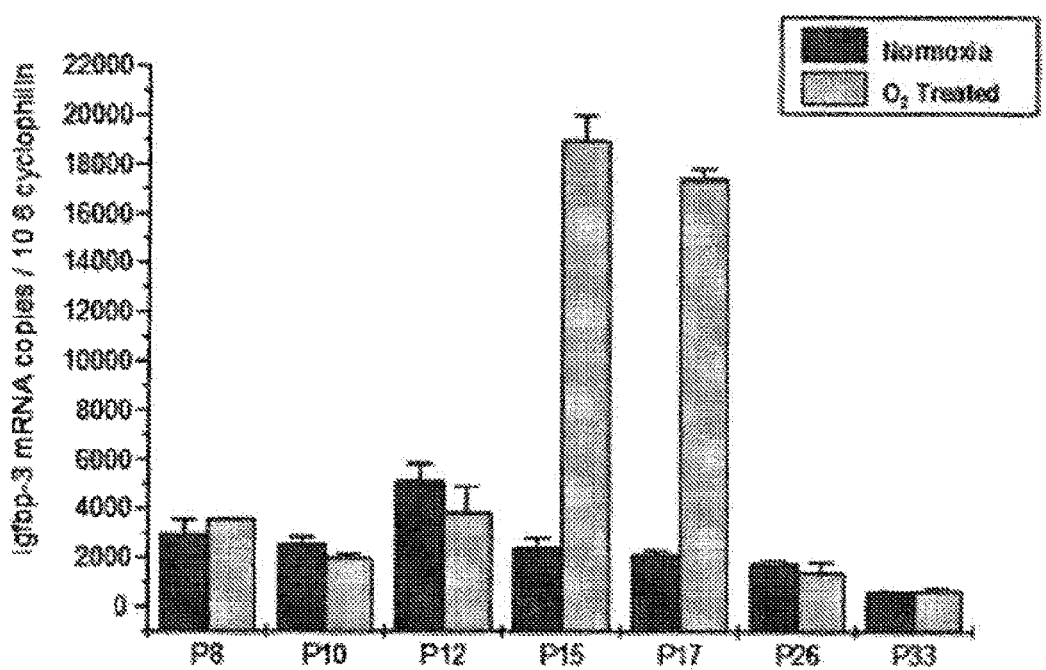
FIG. 6 shows that IGFBP-3 mRNA in whole retina increases with hypoxia.

The onset of hypoxia occurs at P12 when mice are returned to room air after oxygen-induced retinal vessel loss. There is a 3 to >9 fold increase in IGFBP-3 mRNA in whole retina between P12 and P15 persisting through P17 that decreases by P26 when hypoxia is relieved with re-vascularization (n=12 retinas per condition). In FIG. 6 each bar represents IGFBP-3 mRNA copy number normalized to one million copies of cyclophilin (an unchanged control gene).

EXAMPLE 7

IGFBP-3 mRNA is Localized to Retinal Vascular Areas

Figure 7:
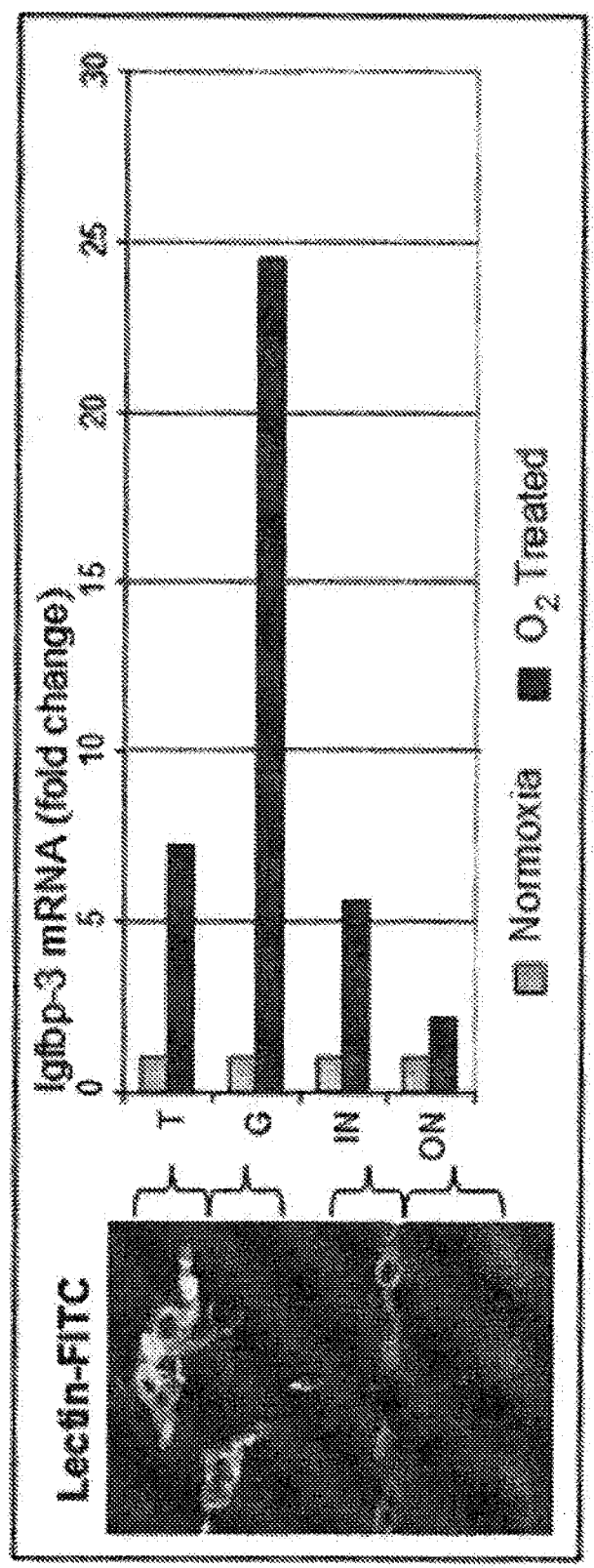
FIG. 7 shows that IGFBP-3 mRNA is associated with retinal blood vessels and increases with hypoxia.

IGFBP-3 mRNA is localized to areas of retinal neovascularization (tufts) extending into the vitreous at P17 and to the ganglion cell layer and inner nuclear layer where vessels are located. Within the local vascular areas IGFBP-3 mRNA increases between 5 and 25 fold with hypoxia at P17. In the avascular photoreceptor layer there is only a small increase in IGFBP-3 mRNA with hypoxia at P17 compared to non-oxygen treated controls. In FIG. 7 it is seen that IGFBP-3 mRNA is associated with retinal blood vessels and increases with hypoxia. Quantitative real time RT-PCR analysis of IGFBP-3 mRNA analyzed from laser captured areas of retinal blood vessels shows a large increase in IGFBP-3 mRNA in the superficial vascular layers at P17 with hypoxia, indicating that IGFBP-3 is associated with retinal blood vessels and not with surrounding tissue. T: neovascular vessel tufts extending into the vitreous, G: ganglion cell layer, ON: outer nuclear layer, IN: inner nuclear layer.

EXAMPLE 8

Decreased Number of Endothelial Progenitor Cells (EPC) in the Retina of IGFBP3−/− Mice IGFBP-3$^{-/-}$ and wild type control litters were exposed to 75% oxygen from P7 to P12, and then moved to room air. Animals were sacrificed on P15. Retinas from IGFBP-3$^{-/-}$ (n=8 eyes) and IGFBP-3$^{+/+}$ mice (n=7 eyes) were isolated and fixed in 4% paraformaldehyde for 1 hr, permeabilized in PBS with 1% Triton X-100 overnight, followed by *Griffonia simplicifolia* lectin I (endothelial cell specific) (Invitrogen, Eugene, Oreg., USA) and CD34-FITC antibody (Miltenyi Biotec Inc. Auburn, Calif., USA) staining.

Figure 8:
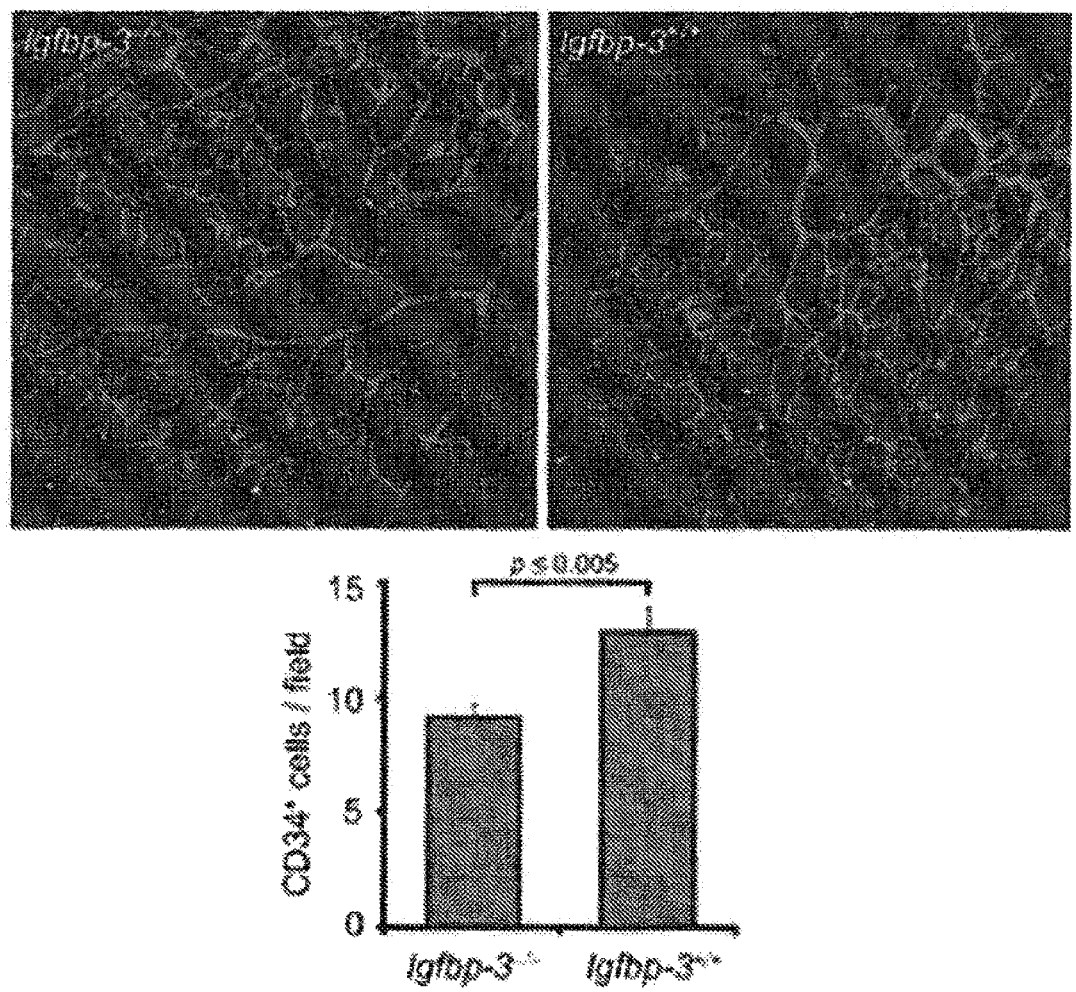
FIG. 8 shows a decreased number of Endothelial Progenitor Cells (EPCs) in the retinal of IGFBP-3 null mice.

To evaluate the effect of IGFBP-3 on EPC recruitment into retina, we examined at P15 retinas from IGFBP3−/− mice after oxygen induced retinopathy. EPCs are identified with CD34 antibody staining. Compared with wild type animal (n=7), in the retina of IGFBP3−/− mice (n=8) there are almost 30% less CD34+ cells in the retina (P=0.003). In FIG. 8 it is seen that Quantification of CD34+ cells in the retina of P15H IGFBP-3$^{-/-}$ mice at P15H (n=8) revealed a significant decreased number of EPCs compared with wild type animal (n=7, P=0.003). Red: lectin-Alexa 594 (endothelial cell specific), Green: CD34-FITC antibody. This suggests that IGFBP-3 may contribute to retinal vessel repair by recruiting bone marrow-derived EPCs into the site of injury.

EXAMPLE 9

In a Clinical Study Increased Serum IGFBP-3 Correlates with Less Severe ROP

Infants born at gestational age (GA)<32 weeks were recruited at the Queen Silvia Children's Hospital in Goteborg and at Uppsala University Hospital (190 eligible, 79 enrolled between December 1999 and April 2002. Inability to complete postnatal follow-up until post-menstrual age (PMA) 40 weeks or discharge to home and conspicuous congenital anomaly were exclusion criteria. The group included 19 twins, 8 pairs and 3 whose siblings died. All infants were hospitalized in a neonatal intensive care unit. Enteral feeding with increasing amounts of breast milk was introduced early (2-48 hours after birth). Until full enteral feeding was achieved supplementary parenteral nutrition with glucose, amino acids, and fat was given. Breast milk fortified with 0.8 g of protein/100 ml was given to infants <1500 g from ~10 days PMA until the infant weighed 2000 g. The Ethics Committees of the Medical Faculties at Goteborg and Uppsala Universities gave approval (#Ö594-00), and informed consent was obtained from parents.

Dilated retinal examinations with indirect ophthalmoscopy were performed weekly or biweekly from the age of 5 to 6 weeks after birth until the retina was fully vascularized or the condition was considered stable. Children with plus disease and/or stage 3 ROP had more frequent examinations. ROP changes were classified according to the International Classification of ROP.

Weekly blood samples (0.5 ml) for each infant were stored at −20° C. to −80° C. and assayed at the same time. Serum IGFBP-3 levels were measured using a specific radioimmunoassay (RIA) for IGFBP-3 (Mediagnost GmbH, Tübingen, Germany). For the IGFBP-3 assay, the intraassay coefficient of variation (CV) were 7.1, 7.3, and 7.9% at concentrations of 1800, 3790, and 5776 µg/L, respectively, and the interassay CVs were 13.4, 10.5, and 14.1%.

Figure 9:
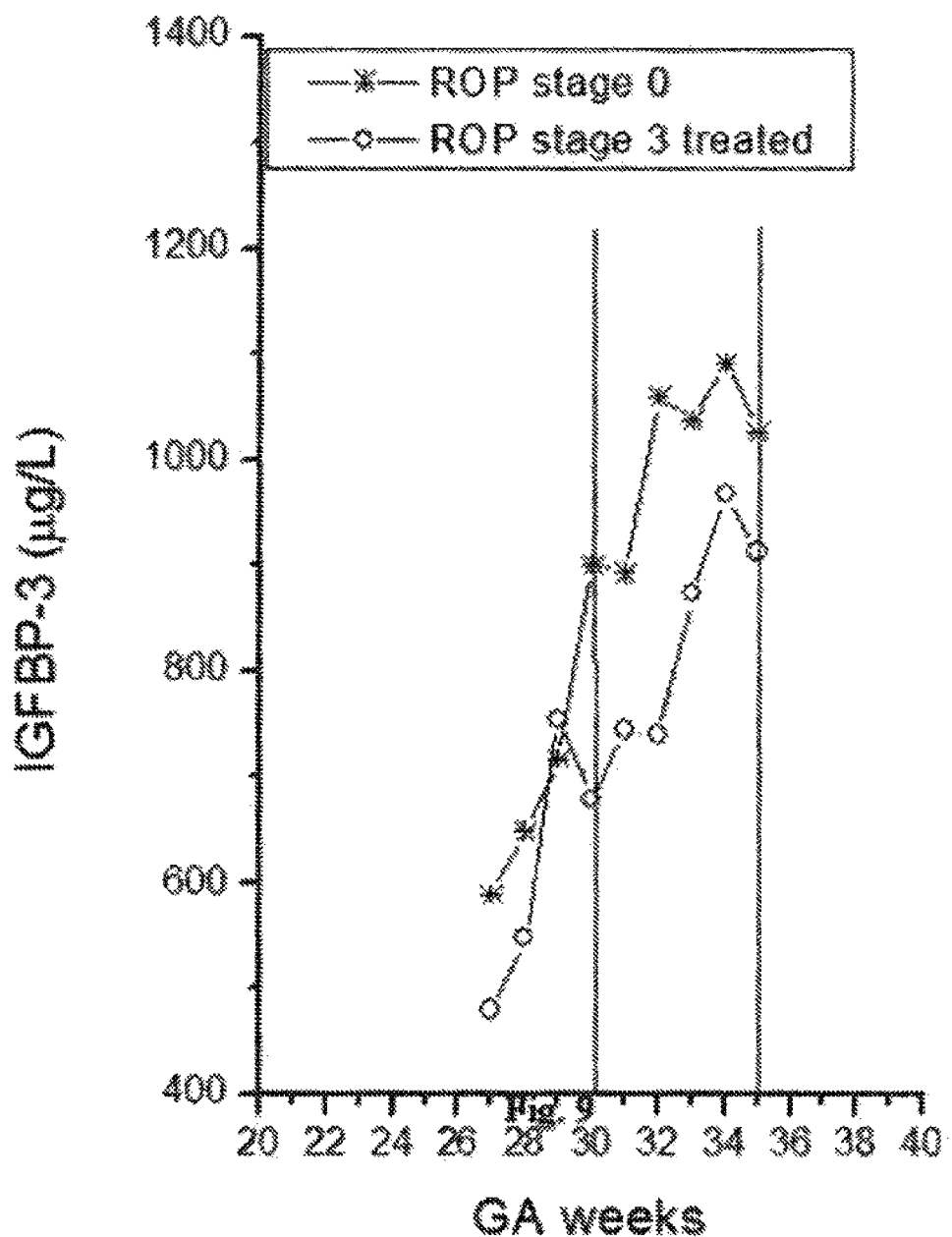
FIG. 9 shows that higher serum levels of IGFBP-3 are associated with reduction in ROP in children.

To test the hypothesis that increased IGFBP-3 levels after birth protect against vessel loss and therefore against proliferative ROP in premature infants, we prospectively measured IGFBP-3 plasma levels weekly after birth and coordinately examined retinas in all premature infants born at gestational ages <32 weeks at high risk for ROP (n=79). ROP stages 0-4 were defined according to the International Classification, and, for these studies ROP stages 3-4 (n=13) were defined as proliferative ROP and ROP stage 0 (n=38) as no ROP. We confirmed that lack of vascular growth is associated with proliferative ROP. The normal immature retina has a gradual transition from translucent vascularized retina into gray, nonvascularized retina without a distinct border between the two. In ROP, a sharp observable stationary border consisting of a line or ridge between vascularized and nonvascularized retina becomes apparent. In all patients with proliferative ROP (n=13), there was a demarcation line anterior to which no vessels were seen. In all infants with no ROP (n=38), there was no ridge and no demarcation line, indicating more normal growth of the vascular front (data not shown). The mean±SEM level of IGFBP-3 at 30-35 weeks postmenstrual age for infants with proliferative ROP was 802±66 µg/L and for infants with no ROP was 974±41 µg/L. The Mann-Whitney Test yielded a P value of 0.03, indicating a significant difference between the two groups in mean IGFBP-3 at this time point (FIG. 9).

From the above examples it can be seen that increasing levels of IGFBP-3 are associated with decreased retinal neovascularization (ROP) and therefore with increased normal vascular growth. In the studies using IGFBP-3$^{-/-}$ transgenic mice and in other studies utilizing supplemental recombinant IGFBP-3 in wild type mice, it is determined that there is a dose response of pathological retinal neovascularization to decreasing IGFBP-3 levels in vivo. Increasing levels of IGFBP-3 decreases retinal vascular loss, increases vessel re-growth and thereby decreases neovascularization. Furthermore, the protective effect of IGFBP-3 appears to be independent of IGF-I since serum IGF-I levels in transgenic and wild type mice were the same and adding exogenous IGFBP-3 above the normal level further promoted vessel re-growth. Although IGFBP-3 actions have been studied in vitro, there is few, if any, experimental studies in vivo that directly address the role of IGFBP-3 in vascular development.

In the clinical study in premature infants described above in Example 9, it is also shown that low levels of serum IGFBP-3 between PMA weeks 30-33 (when induction of ROP occurs) is correlated with increased risk of developing proliferative ROP. These data correspond to earlier findings that premature infants with low levels of IGF-I in early development have less vascular growth and an increased risk of ROP. Interestingly, it is observed that the IGF-I/IGFBP-3 ratio is similar between premature infants who develop proliferative ROP and those who do not (data not shown). Moreover there were no significant differences in acid labile subunit levels between non-ROP and ROP children (data not shown), suggesting that the critical factors in the serum IGF1 complex (IGF1, IGFBP-3 and acid labile subunit) are both IGF1 and IGFBP3. This suggests that restoring both IGF-I and IGFBP-3 levels simultaneously in children at risk of developing ROP and thereby keeping the IGF-I/IGFBP-3 ratio intact is critically important in preventing destructive retinal neovascularization (ROP). IGFBP-3 is today available as rhIGF-I/rhIGFBP-3 combination.

The mechanism by which IGFBP-3 helps prevent vessel loss and improves repair is likely to be multifactorial. The relative contribution of systemic versus local IGFBP3 is not known. However, IGFBP-3 mRNA is found in the retinal vasculature and increases substantially with hypoxia. This local source may play a significant role in controlling vascular growth. However, since IGFBP-3 promotes the growth of stem cells in vitro, it can be speculated that stem cell recruitment to blood vessels may be stimulated by increasing IGFBP-3 levels. In Example 8 it is shown that deficiency of IGFBP-3 is associated with decreased number of CD34+ EPCs in the retina, suggesting that IGFBP-3 might improve vessel repair by promoting the incorporation of bone marrow-derived EPCs into the retina. This recruitment might stabilize and normalize the retinal vasculature.

Patients with ROP or diabetes are susceptible to retinal vascular loss that can then precipitate hypoxia-induced proliferation of blood vessels, causing retinal detachments and blindness. Interventions that prevent vessel loss or promote efficient vessel re-growth can prevent pathologic neovascularization as well as many complications of diabetes that involve vascular loss, such as heart disease. These findings are likely to apply to other disease pathologies involving the regulation of vascular networks.

IGF-I has been suspected to be involved in diabetic retinopathy for decades, but clinical studies of a correlation have had varied results. In one study, however, patients with type 1 diabetes had reduced serum levels of IGFBP-3 (and free plus dissociable IGF-I) compared to non diabetic controls (Frystyk, J., Bek, T., Flyvbjerg, A., Skjaerbaek, C. & Orskov, H. (2003) *Diabet Med* 20, 269-76.). Patients with proliferative retinopathy have increased vitreous levels of IGF-I and IGFBP-3 as well as other binding proteins thought to be due to increased vascular leakage.

In summary, premature infants with lower levels of serum IGFBP-3 are at greater risk for retinopathy. In the mouse model of ROP the protective effect of IGFBP-3 appears to be independent of IGF-I and is a result of increased protection against vessel loss and increased re-growth of vessels after damage. The mechanism of vascular stabilization is consistent with recruitment of endothelial precursor cells. These results have significant implications for treatment of patients with diabetes and ROP, diseases associated with vascular loss and subsequent destructive neovascularization. Improved vascularization of the retina will tend to decrease the hypoxic stimulus required for later development of pathological neovascularization, reducing the degree of ROP. This work suggests that restoring not only IGF-I but also IGFBP-3 levels simultaneously in children at risk for developing ROP would have similar protective effects and thereby keeping the IGF-I/IGFBP-3 ratio intact is critically important in preventing destructive retinal neovascularization (ROP).

Therefore, the present invention provides, in one aspect, a method for treating a patient suffering from a complication of preterm birth, very preterm birth and/or extremely preterm birth or preventing a patient from developing a complication of preterm birth, very preterm birth and/or extremely preterm birth, said complications being developmental delay, mental retardation, bronchopulmonary dysplasia, intraventricular hemorrhage and retinopathy of prematurity (ROP). The method involves administering to a patient having a serum level of IGF-I and/or IGFBP-3 below the norm for in utero levels, an effective amount of IGF-I or an analog thereof in combination with IGF-I binding protein 3 (IGFBP-3) or an analog thereof, to elevate the patient's IGF-I and IGFBP-3 levels to ranges corresponding to normal in utero levels for the patient's gestational age. These levels are for IGF-I and IGFBP-3 in the ranges of 10 to 100 and 500 to 1 400 µg/L respectively depending on the patient's gestational age. The IGF-I and IGFBP-3 or analogs thereof may be administered subcutaneously, intravenously or orally. Intravenous administration is preferred.

It is preferred that the methods of the present invention be initiated soon after birth in order to effectively prevent complications of prematurity and to promote normal vascular development. This is especially critical for the treatment of ROP, wherein increasing IGF-I levels may promote the late neovascular, destructive phase of ROP. The treatment which is delayed until after the non-vascularized retina becomes hypoxic might trigger abnormal retinal neovascularization.

Administration of IGF-I or an analog thereof in combination with IGFBP-3 or an analog thereof results in increases in circulating levels of IGF-I and IGFBP-3. Accordingly, administration of IGF-I in combination with IGFBP-3 is useful for the treatment or prevention of symptoms, disorders, and conditions associated with low circulating levels of IGF-I and or IGFBP-3.

The inventive methods disclosed herein provide for the parenteral administration of IGF-I in combination with IGFBP-3 complex to infants in need of such treatment. Parenteral administration includes, but is not limited to, intravenous (IV), intramuscular (IM), subcutaneous (SC), intraperitoneal (IP), intranasal, microdialysis and inhalant routes. In the method of the present invention, IGF-I and IGFBP-3 or analogs thereof are preferably administered orally. IV, IM, SC, and IP administration may be by bolus or infusion, and may also be by slow release implantable device, including, but not limited to pumps, slow release formulations, and mechanical devices. The formulation, route and method of administration, and dosage will depend on the disorder to be treated and the medical history of the patient. In general, a dose that is administered by subcutaneous injection will be greater than the therapeutically-equivalent dose given intravenously or intramuscularly. The composition for use in accordance with the present invention has a ratio providing and maintaining, in the patient, a normal physiological ratio corresponding to the endogenous molar ratio of the patient correlated for the patient's gestational age or will correct an abnormal ratio of IGF-I/IGFBP-3. The dose range of IGF-I is from 5 to 450 µg/kg per 24 hours irrespective mode of administration. The dose is easily determined in each specific case by a person skilled in the art based on the patient's weight and/or gestational age and/or the measured of IGF-I and/or IGFBP-3 level in the patient. More preferably, the dose of IGF-I or an analog thereof is from about 5 µg/kg to about 370 µg/kg per 24 hours.

The composition according to the invention should comprise both IGF-I and IGFBP-3 wherein the IGF-I/IGFBP-3 molar ratio is lower than equimolar preferably in the range from 1:20 to 1:3.33, e.g. 1:20 to 1:4, 1:15 to 1:5 or 1:12 to 1:8. The preferred form is a therapeutic composition of corresponding to the endogenous molar ratio of the patient correlated for the patient's gestational age, where such ratio of rhIGF-I/rhIGFBP-3 ranges from 1:20 to 1:3.33 with the preferred intervals listed above.

The composition can be administered to the patient as a fixed combination in a ratio which is lower than equmolar preferably from 1:3.33 to 1:20, e. g. 1:4, 1:5, 1:8, 1:12, 1:15, 1:18; or IGF-I and IGFBP-3 can be administered separately within the ratio from 1:3.33 to 1:20 to achieve the correct ratio of IGF-I and IGFBP-3 in the patient; or IGF-I and IGFBP-3 can be administered to the patient as a fixed combination, as described above, supplemented with separately administered IGFBP-3 to achieve the correct ratio in the patient.

The composition is administered or is initiated not later than five days post-birth, preferably not later than four days post-birth, more preferably not later than three days post-birth, most preferably not later than two days post-birth.

Preferably the combination is dissolved in physiologically compatible carriers such as normal saline, or phosphate buffered saline solution. More preferably, a concentrated solution of recombinant human IGF-I and a concentrated solution of recombinant human IGFBP-3 are mixed together for a sufficient time to form an equimolar complex. Most preferably, recombinant human IGF-I and recombinant human IGFBP-3 are combined to form a complex during purification, as described in International Patent Application No. WO96/40736.

For parenteral administration, compositions of the complex may be semi-solid or liquid preparations, such as liquids, suspensions, and the like. Physiologically compatible carriers include, but are not limited to, normal saline, serum albumin, 5% dextrose, plasma preparations, and other protein-containing solutions. Optionally, the carrier may also include detergents or surfactants.

In yet another aspect of the invention there is provided use of an IGF-I or analog thereof in the manufacture of a therapeutic composition for treating a complication of preterm birth.

Finally, there is also provided an article of manufacture comprising packaging material and a pharmaceutical agent contained within the packaging material. The packaging material comprises a label which indicates that the pharmaceutical may be administered, for a sufficient term at an effective dose, for treating and/or preventing complications associated with preterm birth. The pharmaceutical agent comprises IGF-I or an analog thereof together with a pharmaceutically acceptable carrier.

For therapeutic applications, IGF-I or an analog thereof may be suitably administered to a patient, alone or as part of a pharmaceutical composition, comprising the IGF-I or an analog thereof together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, nasal, topical (including buccal and sublingual), or parenteral (including subcutaneous, intramuscular, intravenous, microdialysis and intradermal) administration. The formulations may conveniently be presented in unit dosage form, e.g., tablets and sustained release capsules, and in liposomes, and may be prepared by any methods well know in the art of pharmacy. See, for example, *Remington's Pharmaceutical Sciences*, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. A method for reducing the risk of developing a complication of preterm birth comprising administering to a preterm infant having a serum level of IGF-1 and IGFBP-3 below the in utero normal for the same gestational age, an effective amount of IGF-1 in combination with IGFBP-3, wherein the molar ratio of IGF-1 to IGFBP-3 is lower than equimolar, in the range from 1:20 to 1:3.33, thereby elevating the preterm infant's IGF-1 and IGFBP-3 serum levels to normal in utero levels, wherein the complication of preterm birth is selected from the group consisting of bronchopulmonary dysplasia, intraventricular hemorrhage and retinopathy of prematurity (ROP).

2. The method of claim 1, wherein the complication of preterm birth is bronchopulmonary dysplasia.

3. The method of claim 1, wherein the complication of preterm birth is retinopathy of prematurity.

4. The method of claim 1, wherein said administering is initiated not later than three days post-birth.

5. The method of claim 1, wherein said administering is initiated not later than five days post-birth.

6. The method of claim 1, wherein the combination of IGF-I and IGFBP-3 is administered intravenously or by inhalation.

7. The method of claim 1, wherein the IGFBP-3 is recombinant human IGFBP-3 (rhIGFBP-3).

8. The method of claim 1, wherein the IGF-I is recombinant human IGF-I (rhiGF-I).

9. The method of claim 1, wherein the molar ratio of the IGF-I to IGFBP-3 administered is within the range of from 1:15 to 1:5.

* * * * *